(12) United States Patent
Son et al.

(10) Patent No.: US 12,050,211 B2
(45) Date of Patent: Jul. 30, 2024

(54) DEVICE AND METHOD FOR QUANTITATIVE EVALUATION OF DEODORANT PERFORMANCE

(71) Applicant: LG Chem, Ltd., Seoul (KR)

(72) Inventors: Jihyang Son, Daejeon (KR); Min Hwan Jung, Daejeon (KR); Jin Woo Lee, Daejeon (KR)

(73) Assignee: LG Chem, Ltd., Seoul (KR)

( * ) Notice: Subject to any disclaimer, the term of this patent is extended or adjusted under 35 U.S.C. 154(b) by 742 days.

(21) Appl. No.: 17/271,003

(22) PCT Filed: Apr. 9, 2020

(86) PCT No.: PCT/KR2020/004814
§ 371 (c)(1),
(2) Date: Feb. 24, 2021

(87) PCT Pub. No.: WO2020/235808
PCT Pub. Date: Nov. 26, 2020

(65) Prior Publication Data
US 2021/0325353 A1    Oct. 21, 2021

(30) Foreign Application Priority Data

May 17, 2019    (KR) .................. 10-2019-0057937
Apr. 8, 2020    (KR) .................. 10-2020-0042482

(51) Int. Cl.
*B01L 3/00*        (2006.01)
*B01F 23/00*       (2022.01)
(Continued)

(52) U.S. Cl.
CPC ............. *G01N 30/72* (2013.01); *G01N 30/12* (2013.01); *G01N 30/68* (2013.01); *G01N 30/70* (2013.01);
(Continued)

(58) Field of Classification Search
CPC ........ G01N 30/72; G01N 30/12; G01N 30/68; G01N 30/70; G01N 30/88; G01N 33/0054;
(Continued)

(56) References Cited

U.S. PATENT DOCUMENTS

| | | |
|---|---|---|
| 10,583,052 B2 | 3/2020 | Lee et al. |
| 2018/0228670 A1 | 8/2018 | Lee et al. |

(Continued)

FOREIGN PATENT DOCUMENTS

| | | | | |
|---|---|---|---|---|
| CN | 104628012 A | * | 5/2015 | |
| EP | 3321313 A1 | * | 5/2018 | ............. A61F 13/53 |

(Continued)

OTHER PUBLICATIONS

Proceeding of the 34th Meeting of KOSAE (2002) Korean Society for Atmospheric Enviroment 2002, p. 70-71.

(Continued)

*Primary Examiner* — Jennifer Wecker
*Assistant Examiner* — Oyeleye Alexander Alabi
(74) *Attorney, Agent, or Firm* — Lerner David LLP

(57) ABSTRACT

The present invention relates to a device and a method for evaluating performance of a deodorant using a superabsorbent polymer (SAP), and the device and method are capable of quantitatively evaluating deodorant performance by collecting ammonia adsorbed to deodorant materials including the SAP and measuring the amount of ammonia thereof.

7 Claims, 3 Drawing Sheets

(51) Int. Cl.
  *B01F 23/41* (2022.01)
  *B01F 101/23* (2022.01)
  *B23Q 17/24* (2006.01)
  *C12M 1/34* (2006.01)
  *C12Q 1/18* (2006.01)
  *G01N 21/3577* (2014.01)
  *G01N 21/359* (2014.01)
  *G01N 21/39* (2006.01)
  *G01N 21/45* (2006.01)
  *G01N 21/64* (2006.01)
  *G01N 30/12* (2006.01)
  *G01N 30/68* (2006.01)
  *G01N 30/70* (2006.01)
  *G01N 30/72* (2006.01)
  *G01N 30/88* (2006.01)
  *G01N 33/00* (2006.01)
  *G01N 33/50* (2006.01)
  *G01N 33/68* (2006.01)

(52) U.S. Cl.
  CPC ......... *G01N 30/88* (2013.01); *G01N 33/0054* (2013.01); *G01N 2030/885* (2013.01)

(58) Field of Classification Search
  CPC ..... G01N 2030/885; G01N 2033/0088; G01N 1/405; G01N 2030/8809; G01N 30/7206; G01N 30/96; G01N 2030/025; G01N 2030/128; G01N 2030/645; Y02A 50/20
  See application file for complete search history.

(56) References Cited

U.S. PATENT DOCUMENTS

2019/0107527 A1    4/2019  Choi et al.
2022/0221397 A1*   7/2022  Abe ................... G01N 33/0073

FOREIGN PATENT DOCUMENTS

| JP | 2000019119 A | | 1/2000 | |
| JP | 2001013119 A | | 1/2001 | |
| JP | 2003075418 A | | 3/2003 | |
| JP | 3887504 B2 | * | 2/2007 | |
| JP | 2008008788 A | * | 1/2008 | |
| JP | 2008008788 A | | 1/2008 | |
| JP | 2012112880 A | | 6/2012 | |
| JP | 2016170068 A | | 9/2016 | |
| JP | 2017221488 A | | 12/2017 | |
| KR | 20020062233 A | | 7/2002 | |
| KR | 20100026685 A | | 3/2010 | |
| KR | 20170068384 A | | 6/2017 | |
| KR | 20180074387 A | | 7/2018 | |
| WO | WO-2019196486 A1 | * | 10/2019 | ......... B01D 53/0438 |

OTHER PUBLICATIONS

International Search Report for PCT/KR2020/004814 mailed Jul. 14, 2020; 3 pages.

* cited by examiner

[Fig. 1]
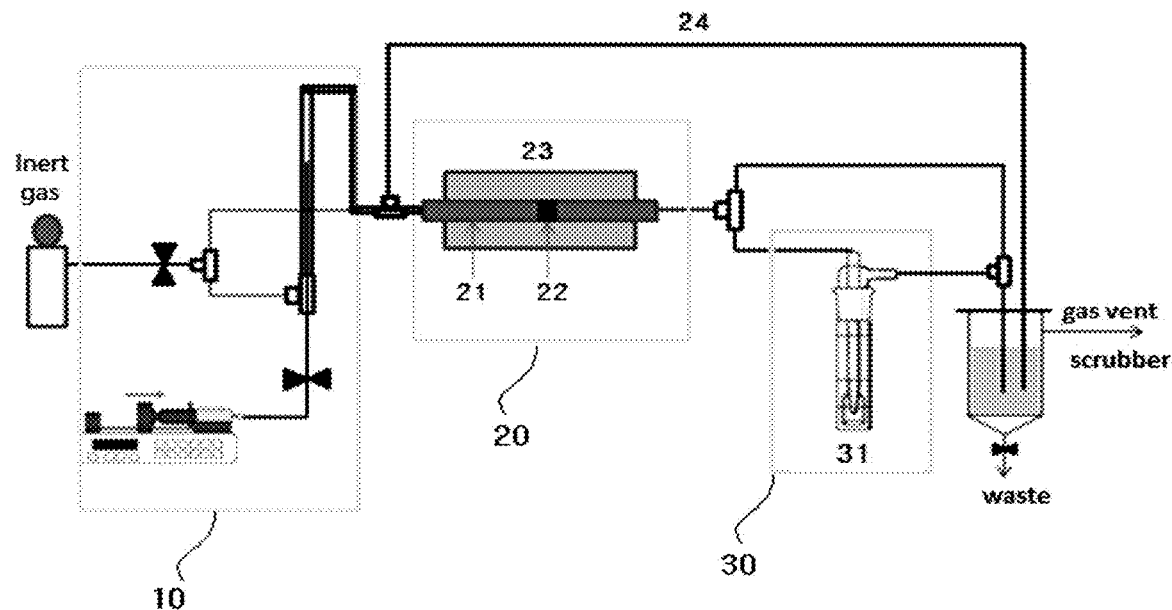
[Fig. 2]
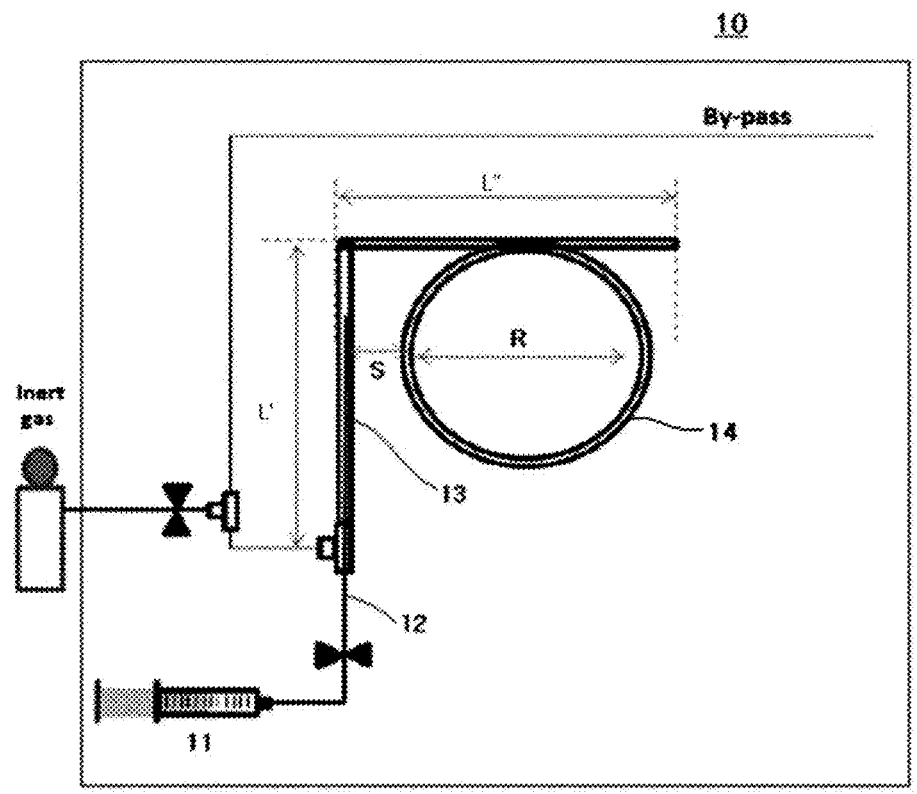

[Fig. 3]
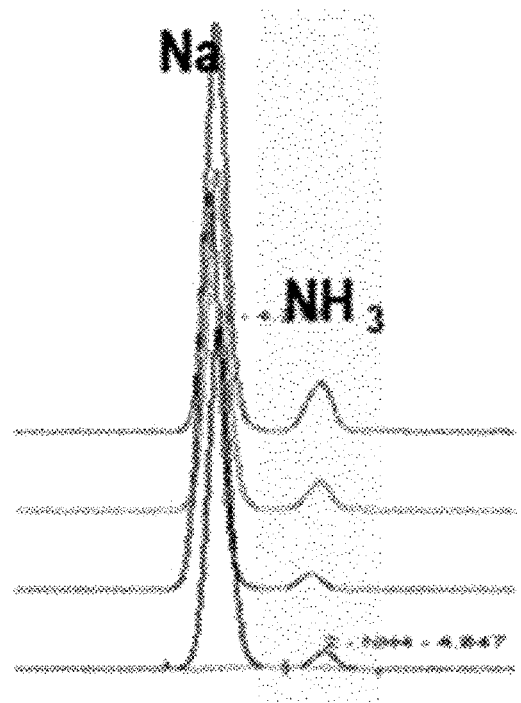
[Fig. 4]
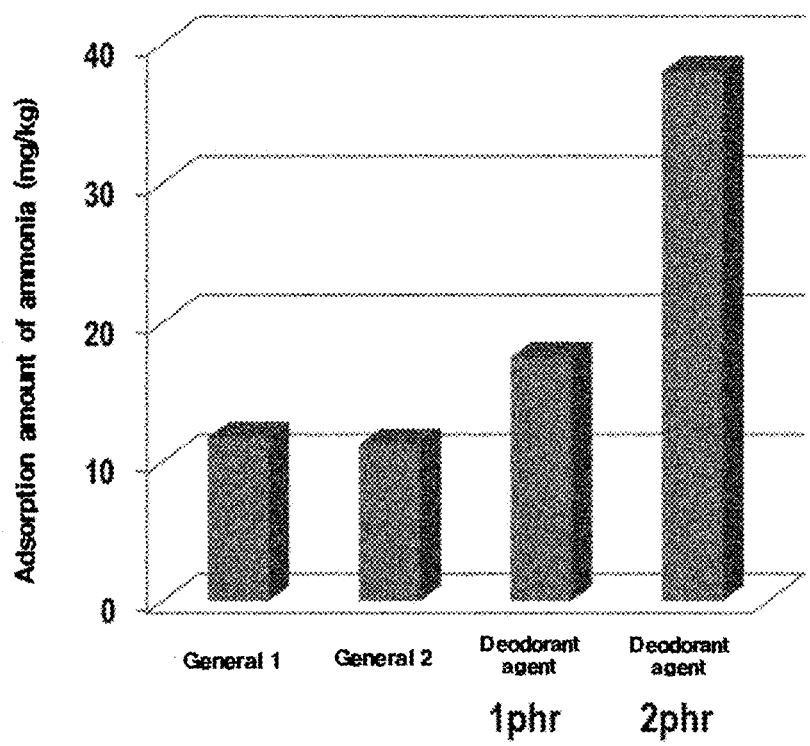

[Fig. 5]
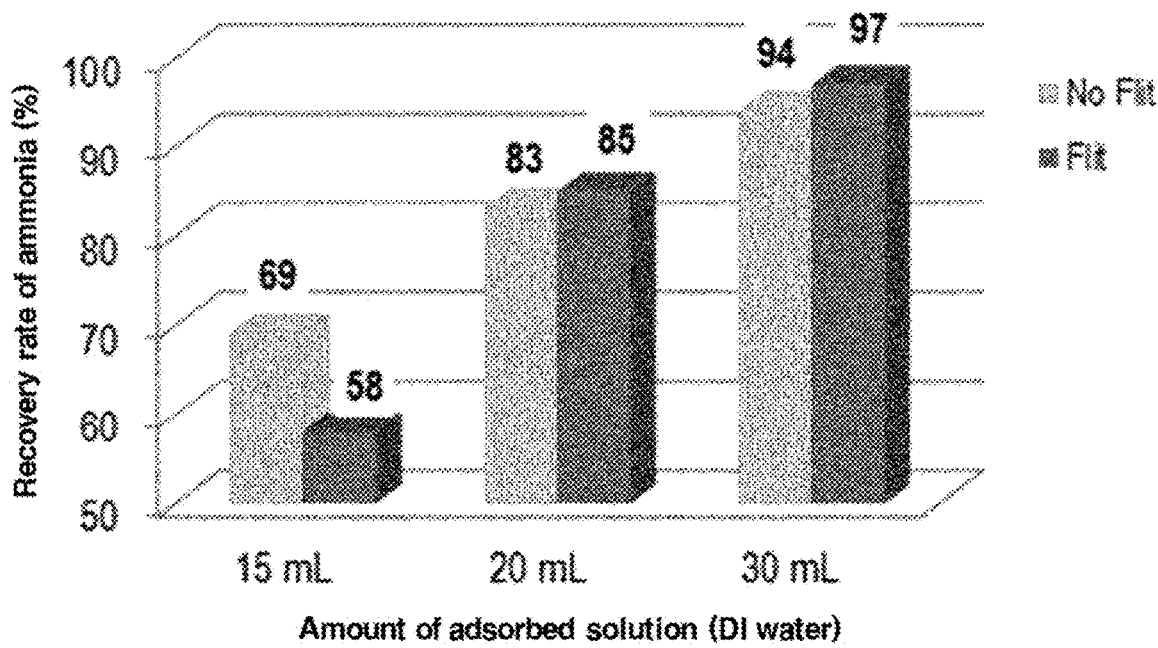

DEVICE AND METHOD FOR QUANTITATIVE EVALUATION OF DEODORANT PERFORMANCE

CROSS-REFERENCE TO RELATED APPLICATIONS

The present application is a national phase entry under 35 U.S.C. § 371 of International Application No. PCT/KR2020/004814, filed on Apr. 9, 2020, which claims priority to Korean Patent Application No. 10-2019-0057937 filed on May 17, 2019 and Korean Patent Application No. 10-2020-0042482 filed on Apr. 8, 2020, the disclosures of which are incorporated herein by reference in their entirety.

TECHNICAL FIELD

The present invention relates to an apparatus and method for quantitatively evaluating a deodorant performance using a superabsorbent polymer (SAP).

BACKGROUND OF THE INVENTION

A superabsorbent polymer (SAP) is a polymer that has a three-dimensional network structure and has a large amount of hydrophilic groups that can absorb much quantity of water without being dissolved in water, and thus is widely used for a soil repair material for gardening, a civil engineering, a water supply material for construction, a sheet for raising seedlings, a freshness retention material in food distribution field, and a material for poultice, etc., in addition to a hygiene product such as a paper diaper and a sanitary ware.

In recent years, high value performance such as a deodorant performance has been introduced into these SAP products to create differentiated products. In particular, the deodorant function in the products such as the diaper and the sanitary ware is an important factor in accordance with a promotion of cleanliness sense.

Conventionally, the deodorant performance was analyzed in a method such as a detection tube manner. The detection tube manner is a method that consists of filling a thin glass tube with an inner diameter of 2 to 4 mm by absorbing a reagent discoloring when reacting with an analytical target into a silica gel, and then observing a degree of discoloration of the silica gel by passing the analytical target gas through the thin glass tube. However, since this detection tube manner uses the discoloration caused by a chemical reaction, there is a problem that quantification is not very high and precision is poor due to an influence of other substances.

Meanwhile, there is a method for identifying a degree of reduction of a deodorant target material after passing the target material through a deodorant member by a gas chromatography (GC), a mass spectrometry (MS), and the like. However, since this method can be quantified only when a standard gas is contained and the ammonia known as a representative component that emits an odor is classified as a toxic substance, there is a problem in that additional facilities such as a dedicated cabinet and an explosion-proof equipment, a neutralization equipment, etc. must be provided bulkily. In addition, when the ammonia gas is analyzed, since a mass thereof is similar to that of a moisture, it has an additional problem that the analysis is impossible in case the moisture is present in a sample.

Therefore, there is a need for an apparatus for evaluating the deodorant performance capable of accurately quantifying a deodorant effect in a simple process without additional facilities.

SUMMARY OF THE INVENTION

Technical Challenges

A purpose of the present invention is to provide an apparatus for quantitatively evaluating a deodorant performance.

Another purpose of the present invention is to provide a method for quantifying the deodorant performance with an adsorption amount of an deodorant target material using the above apparatus.

Technical Solutions

In order to settle the above problems, the present invention provides an apparatus for quantitatively evaluating performance of a deodorant member, comprising:
a vaporization module for vaporizing an ammonia water;
an adsorption/desorption module connected to the vaporization module and adsorbing and desorbing the vaporized ammonia on a surface of the deodorant member; and
a collection module connected to the adsorption/desorption module and collecting the desorbed ammonia gas,
wherein the adsorption/desorption module includes a reactor, the deodorant member accommodated into the reactor, a tubular kiln for heating the reactor, and a by-pass for injecting a carrier gas into the glass reactor, and
the deodorant member includes a superabsorbent polymer (SAP).

Further, the present invention provides a method for quantitatively evaluating performance of a deodorant member using the above apparatus, the method comprising the steps of:
heating an ammonia to vaporize it;
adsorbing the vaporized ammonia to the deodorant member;
desorbing the ammonia from the deodorant member by injecting a carrier gas into the deodorant member having the ammonia gas adsorbed therein for 5 minutes to 1 hour, and raising a temperature from 100° C. to 700° C. at a rate of 1 to 10° C./min; and
collecting and quantitatively analyzing the desorbed ammonia gas through an impinger,
wherein the deodorant member includes a superabsorbent polymer (SAP).

Furthermore, the present invention provides a system for evaluating a deodorant performance, comprising the above apparatus.

Effect of the Invention

According to the present invention, the deodorant performance can be quantitatively evaluated by collecting an ammonia gas adsorbed into a deodorant member containing a superabsorbent polymer (SAP) and measuring its content.

BRIEF DESCRIPTION OF THE DRAWINGS

FIG. 1 is a schematic diagram showing an apparatus for quantitatively evaluating a deodorant performance according to an embodiment of the present invention.

FIG. 2 is a schematic diagram showing a vaporization module included in the apparatus of FIG. 1.

FIGS. 3 and 4 are graphs showing an adsorption amount of an ammonia to a deodorant member using the apparatus according to an embodiment of the present invention.

FIG. 5 is a graph showing change in a recovery rate of an ammonia according to an amount of a collected solution.

DETAILED DESCRIPTION OF THE INVENTION

The present invention, which can be applied to various modifications and can have various embodiments, will be described in detail through the specification with reference to the drawings illustrating specific embodiments. However, this is not intended to limit the present invention to the specific embodiments. It should be understood that the present invention includes all modifications, equivalents, and substitutes belonging to the spirit and the technical scope of the present invention. In the description of the present invention, if it is considered that a detailed description of known technologies related to the present invention may obscure the subject matters of the present invention, the detailed description will be omitted.

When a constitutive element is referred to as being "connected" or "linked" to the other constitutive element in the present specification, it should be understood that the constitutive element may be directly connected or linked to the other constitutive element or the other constitutive element may be exist in the middle.

In this specification, a singular expression includes a plural expression unless otherwise specified.

The terms such as "comprise", "provide" or "have" in the present specification refer to the presence of features, numerical values, steps, operations, constitutive elements, parts, or combinations thereof described in the specification, and do not exclude the possibility that other features, numerical values, steps, operations, constitutive elements, parts, or combinations thereof which are not mentioned in the specification may exist or be added.

Hereinafter, an apparatus for quantifying performance of a deodorant member according to an embodiment of the present invention will be described in more detail.

An embodiment of the present invention relates to an apparatus for quantitatively evaluating a deodorant performance.

Referring to FIG. 1, an apparatus 100 for quantitatively evaluating deodorant performance according to an embodiment of the present invention may comprise a vaporization module 10 for vaporizing an ammonia water; an adsorption/desorption module 20 having a deodorant member 22 accommodated in a reactor 21; and a collection module 30. In this case, the deodorant member may include a superabsorbent polymer (SAP) material.

The above apparatus 100 makes it possible to quantitatively evaluate the deodorant performance of the deodorant member by heating a syringe pump and a line tube in the vaporization module 10 to vaporize an ammonia, adsorbing the vaporized ammonia to the deodorant member in the adsorption/desorption module 20 connected to the vaporization module 10 followed by desorbing the ammonia through an elevated temperature process under a carrier gas atmosphere, collecting the desorbed ammonia in the collection module 30 connected to the adsorption/desorption module 20 using an impinger 31, and then measuring a content of the collected ammonia. Meanwhile, the carrier gas passing through the impinger 31 is exhausted through a scrubber.

Hereinafter, each module constituting the apparatus 100 will be described in detail.

With reference to FIG. 2, the vaporization module 10 in the apparatus 100 for quantitatively evaluating performance of the deodorant member according to the present invention may include a syringe pump 11; a first stainless tube 12 connected to a syringe tip of the syringe pump; a second stainless tube 13 having the first stainless tube 12 inserted therein; a heating band 14 surrounding the second stainless tube; and a gas injection unit 15 for injecting the carrier gas into the second stainless tube.

The syringe pump 11 is to inject an ammonia water, and may, for example, be provided with a syringe having a 30 ml capacity of polyethylene (PE) material. The first stainless tube 12 of 1/16" may be connected to a tip of the syringe pump and inserted inside the second stainless tube 13 of 1/4".

The ammonia water injected from the syringe pump 11 is supplied to the second stainless tube 13 through the first stainless tube 12, wherein the entire stainless tubes are heated with the heating band 14 and a heating controller to 150° C. or higher, for example, 300° C. or higher, to sufficiently vaporize the ammonia water. A length of the heating band 14 is sufficient as long as it can promote homogeneous mixing with the carrier gas after the ammonia is vaporized, and is not particularly limited.

Meanwhile, an inert gas used as the carrier gas may be mixed with the vaporized ammonia in the second stainless tube 13 through a by-pass.

In an embodiment of the present invention, the injection of the ammonia water may be performed at a rate of 0.005 to 0.5 ml/min, for example, 0.01 to 0.1 ml/min.

The adsorption/desorption module 20 in the apparatus 100 for quantitatively evaluating the deodorant performance according to the present invention may include a reactor 21; a deodorant member 22 accommodated in the reactor; a quartz wool (not shown) located at both ends of the reactor; a tubular kiln 23 for heating the glass reactor; and a by-pass 24 for injecting the carrier gas into the reactor.

The adsorption/desorption module 20 may adsorb an ammonia vaporized in the vaporization module 10 on a surface of the deodorant member 22 accommodated in the glass reactor 21, and then induce desorption of the adsorbed ammonia at an elevated temperature. On the other hand, both ends of the reactor 21 may be filled with the quartz wool to prevent a loss of the superabsorbent polymer due to fluidizing of a gas phase.

The reactor 21 may be the glass reactor and also be heated in the tubular kiln 23. Then, the ammonia water is introduced into the reactor in a trace amount to mix it with the carrier gas followed by stabilizing the mixture by flowing it to the by-pass, and then turning a valve toward the reactor to adsorb the ammonia to the deodorant member.

A desorption process of the ammonia may include blocking inflow of the ammonia water and introducing the carrier gas through the by-pass. The carrier gas may include an inert gas, for example, one or more inert gas selected from the group consisting of a helium, an argon, and a nitrogen, and serve to desorb the ammonia gas physically adsorbed on the surface of the deodorant member.

The tubular kiln 23 heats the reactor 21 so that a temperature of the reactor 21 is raised in the range of 100° C. to 700° C., for example, 300° C. to 600° C., to desorb the ammonia gas adsorbed by chemical bonding on the surface of the deodorant member. If the temperature is lower than 100° C., desorption of the ammonia gas may not be sufficiently achieved, whereas if the temperature exceeds 700° C., the ammonia gas may be decomposed.

The by-pass 24 means an auxiliary tube or a side tube branched from a main tube and connected to the main tube again, and in particular, the introduction of the carrier gas into the by-pass can prevent a condensed ammonia from vaporizing during the desorption process which causes an increase in the analysis error in case a sufficient line purging is not attained with heating in the apparatus.

According to the present invention, the deodorant member includes a superabsorbent polymer (SAP).

The super absorbent polymer (SAP) may be prepared by blending a water-soluble ethylenically unsaturated monomer with any other monomer. For example, the super absorbent polymer may be prepared using one or more selected from the group consisting of an anionic monomer and a salt thereof, a nonionic hydrophilic-containing monomer, and an amino group-containing unsaturated monomer and a quaternary compound thereof. Specifically, the super absorbent polymer may be prepared using one or more selected from the group consisting of an anionic monomer of (meth)acrylic acid, maleic anhydride, fumaric acid, crotonic acid, itaconic acid, 2-acryloylethanesulfonic acid, 2-methacryloylethanesulfonic acid, 2-(meth)acryloylpropanesulfonic acid or 2-(meth)acrylamide-2-methyl propane sulfonic acid, and a salt thereof; a nonionic hydrophilic monomer of (meth)acrylamide, N-substituted (meth)acrylate, 2-hydroxyethyl (meth)acrylate, 2-hydroxypropyl (meth)acrylate, methoxypolyethyleneglycol (meth)acrylate or polyethyleneglycol (meth)acrylate; and an amino group-containing unsaturated monomer of (N,N)-dimethylaminoethyl (meth)acrylate or (N,N)-dimethylaminopropyl (meth)acrylamide, and a quaternary compound thereof. As an example, an alkali metal salt such as an acrylic acid or a salt thereof, for example, an acrylic acid or a sodium salt thereof, may be used to prepare the superabsorbent polymer having a better physical property. In case the alkali metal salt of the acrylic acid is used as the monomer, it can be used by neutralizing the acrylic acid with a basic compound such as a caustic soda (NaOH).

Further, the superabsorbent polymer (SAP) may contain a deodorant agent that gives the deodorant performance, and the deodorant agent may, for example, include, as a material generally used in the art, a porous adsorbent material, a zeolite, an aluminosilicate particle, an aluminosilicate particle carrying an organic acid, an activated carbon, zirconium phosphate, kate, a zinc oxide, and the like, but is not limited thereto. In addition, a shape of the deodorant particle may have a three-dimensional, layered, porous structure, but is not limited thereto.

Furthermore, the deodorant member may include the deodorant agent together with the SAP as described above. As a content of the deodorant agent added to the SAP increases, the deodorant function will improve to increase an adsorption amount of the ammonia to the SAP. This makes it possible to analyze an amount of the used deodorant agent through an amount of the ammonia adsorbed by the deodorant member.

The collection module 30 in the apparatus 100 for quantitatively evaluating performance of the deodorant member according to the present invention may include an impinger 31 and water accommodated in the impinger, for example, a distilled water, an ultrapure water or a deionized water (DI water). The ammonia can be collected by passing a mixed gas of the ammonia and the carrier gas through the impinger containing water, wherein the ammonia is adsorbed into the deodorant member and then desorbed by raising the temperature.

A recovery rate of the ammonia can be improved by increasing an amount of an absorbed solution, i.e., water, to widen an contact area of the mixed gas and water, or a porous flit structure is added to an end portion of the tube where the mixed gas contacts water so that the size of air bubbles can be reduced.

Another embodiment of the present invention relates to a method for quantitatively evaluating deodorant performance using the apparatus as described above. Specifically, the method may comprise the steps of:

heating an ammonia to 100° C. or higher, for example, 150° C. or higher, to vaporize it;

adsorbing the vaporized ammonia to a deodorant member;

desorbing the ammonia from the deodorant member by injecting a carrier gas into the deodorant member having the ammonia gas adsorbed therein for 5 minutes to 1 hour, for example, 10 to 20 minutes, and raising a temperature from 100° C. to 700° C., for example, from 150° C. to 520° C., at a rate of 1 to 10° C./min, for example, 3 to 7° C./min; and collecting and quantitatively analyzing the desorbed ammonia gas through an impinger.

The quantitative analysis of the collected ammonia can be performed using one or more selected from the group consisting of gas chromatography (GC)-thermal conductivity detector (TCD), GC-flame ionisation detector (FID), GC-electron capture detector (ECD), GC-mass spectrometry (MS), and ion chromatography.

In an embodiment of the present invention, a flow rate of the ammonia gas fluidizing to be adsorbed to the deodorant member is not particularly limited, and is 10 to 500 $cm^3$/min as 0.01 to 1% by weight of the ammonia ($NH_3$) in the carrier gas. An adsorption time of the ammonia gas may be 5 minutes or more.

The method for quantifying the deodorant performance according to the present invention can more accurately analyze the deodorant performance of the deodorant member for the ammonia by desorbing, through the heating process, not only the ammonia gas physically weakly bonded but also the ammonia gas chemically strongly adsorbed on the surface of the superabsorbent polymer (SAP) in the deodorant member, to collect and measure all the ammonia gas adsorbed to the deodorant member.

Therefore, according to the present invention, it is possible to quantify a degree of deodorization of the ammonia chemically and physically adsorbed to the deodorant member in a simple process without the need for additional facilities and devices for controlling malodorous substances classified as toxicity.

The present invention further provides a system for evaluating the deodorant performance of the deodorant member, comprising the apparatus as described above.

MODE FOR CARRYING OUT THE INVENTION

Hereinafter, Examples of the present invention will be described in detail so that those skilled in the art to which the present invention pertains can easily practice. However, the present invention can be implemented in many different forms and is not limited to the Examples described herein.

Example 1

In order to evaluate deodorant performance for a deodorant member, the apparatus as shown in FIG. 1 and an ion chromatography (IC) analysis were used.

First, the apparatus of FIG. 1 used for quantitatively evaluating the deodorant performance is as follows.

<Vaporization Module (10)>

As shown in FIG. 2, a vaporization module 10 was prepared to constitute a syringe pump 11 (KDScientific, KDS100 series basic syringe pump, diameter of 22.3 mm, PE), a first stainless tube 12 and a second stainless tube 13 inserted therein (length L' of about 600 mm), a heating band 14, and a gas injection unit 15 for injecting a carrier gas into the second stainless tube. In this case, the heating band 14 was fabricated such that a band of about 3 m in length was wound about three times to form a circle having a diameter (R') of about 250 mm, and a length of L" was about 500 mm in order to secure a space (S) with the second stainless tube 13.

An ammonia water (samchun chmicla) in a concentration of 5000 mg/kg was injected through the syringe pump 11 at a rate of 0.05 ml/min, and supplied to the second stainless tube 13 via the first stainless tube 12. Then, the ammonia water was heated to 150° C. or higher by the heating band 14 to vaporize it, and the vaporized ammonia was mixed with a helium (He) gas which is the carrier gas.

<Adsorption/Desorption Module (20)>

In order to adsorb an ammonia on a surface of the deodorant member 22 containing a superabsorbent polymer (SAP), 0.5 g of the SAP was put into a glass reactor 21 (35 cm, ¼"-1⅜" pyrex), and both ends thereof were filled with a quartz wool to prevent a loss of the SAP due to fluidizing of a gas phase. The glass reactor 21 was placed in a tubular kiln 23 and heated to 150° C. After the ammonia water in a concentration of 5000 mg/kg was introduced to be mixed with 100 ml/min of an inert gas, the mixture was by-passed for 30 minutes to prevent it from passing through the reactor so that the ammonia/carrier gas were stabilized in a uniform state, and then a valve was turned toward the glass reactor to adsorb the ammonia for 1 hour. In this case, the ammonia water was heated to 150° C. from the portion where the ammonia water is introduced to the last portion where a scrubber is located to prevent the ammonia water from condensing.

Then, all of the physically adsorbed ammonia was desorbed by blocking the input of the ammonia water and flowing the helium gas through the by-pass for 15 minutes. Even though all the stainless tubes in the apparatus are heated to 150° C. or higher, if a sufficient line purging is not attained, the possibility of errors in analysis may increase because the condensed ammonia is vaporized during the desorption process. Accordingly, the carrier gas must be introduced through the by-pass upon the desorption. Thereafter, the desorbed ammonia was absorbed into an impinger while raising a temperature from 150° C. to 520° C. at a rate of 5° C./min.

<Collection Module (30)>

In order to evaluate a recovery rate of the ammonia of the gas phase absorbed in a deionized water (DI water), an aqueous ammonia solution having a concentration of 5000 mg/kg was injected with a syringe pump at a rate of 0.05 cc/min, and then vaporized. The recovery rate was confirmed by measuring an ammonia content collected for 30 minutes with the IC by passing a mixed gas of the vaporized ammonia and the He gas through the impinger 31 containing the deionized water.

Meanwhile, the IC used for the analysis was Dionex2100, a column used was IonPac CS12A (4×250 mm)/IonPac CG12A (4×50 mm), a flow rate was 1.0 ml/min, a SRS current was 59 mA, the eluent was methyl sulfonic acid (MSA), and a concentration was measured in 20 mM of isocratic mode.

Further, an adsorption amount of the ammonia was measured using, as the deodorant member, two types of the SAPs having general grade and the SAP containing the deodorant agent added therein, and the results were shown in Table 1, and FIGS. 3 and 4.

TABLE 1

| Grade | Adsorption amount of ammonia (mg/kg) |
|---|---|
| General 1 | 12 |
| General 2 | 11 |
| Deodorant agent 1 phr | 18 |
| Deodorant agent 2 phr | 38 |
| Phr: parts per hundred resin | |

As shown in Table 1, the deodorant performance can be quantified by a simple method of analyzing an adsorption amount of the ammonia adsorbed to the SAP materials containing the deodorant agent and the SAP materials not containing the deodorant agent.

Furthermore, it is expected that an amount of the deodorant agent used for an unknown analytical sample can be analyzed by using the result that an adsorption amount of the ammonia to the SAP increases as an addition amount of the deodorant agent increases.

On the other hand, in order to improve the recovery rate of the ammonia, it may be considered to increase a contact area of the ammonia gas with the deionized water. To this end, the contact surface was tried to be widen by increasing an amount of an absorbed solution, or by equipping a flit filter to an end portion of the impinger 31 included in the collection module 30 so that the size of air bubbles is reduced. The results were shown in FIG. 5.

From FIG. 5, it can be seen that the recovery rate of the ammonia is influenced by the use of the flit filter and the amount of the absorbed solution, and, in particular, depends on the amount of the absorbed solution.

Summarizing these evaluation results, it can be interpreted that the recovery rate is further increased when the flit is applied while the amount of the absorbed solution is increased, and, for example, the effect on the use of the flit is exerted when the amount of the absorbed solution is 20 ml or more. In particular, it was confirmed that about 95% of ammonia can be absorbed when the flit is applied while using 30 ml of the deionized water.

Comparative Example 1

The same product used in the Example was analyzed by a detection tube manner. After a certain volume of ammonia gas was collected into a gas collector (GASTECH, GV-50PS), a detection tube for ammonia analysis (GASTECH, No. 3EL, diameter of 4 mm) was attached to an inlet of the gas collector, and then the collected ammonia gas was passed through the detection tube to observe a degree of discoloration.

As a result, it was confirmed that a degrees of discoloration of the SAP products containing the general SAP 1, the general SAP 2, and the deodorant agent 1 phr were similar to each other due to ambiguous judgment criteria without ensuring reproducibility during repeated experiments, which made it difficult to quantitatively evaluate the deodorant performance.

From the detailed explanation on the specific features of the present invention as described above, it will be obvious to those skilled in the art that these specific technologies are only preferred embodiments, and the scope of the present invention is not limited thereto. Accordingly, the substantial scope of the present invention can be said to be defined by the appended claims and their equivalents.

What are claimed are:

1. An apparatus for quantitatively evaluating performance of a deodorant member, comprising:
   a vaporization module configured to vaporize an ammonia water;
   an adsorption/desorption module connected to the vaporization module, and configured to adsorb and desorb the vaporized ammonia on a surface of the deodorant member; and
   a collection module connected to the adsorption/desorption module, and configured to collect the desorbed ammonia gas,
   wherein the adsorption/desorption module comprises a reactor, the deodorant member accommodated in the reactor, a tubular kiln adapted to heat the reactor, and a by-pass adapted to inject a carrier gas into the reactor, and
   the deodorant member comprises a deodorant agent-containing superabsorbent polymer (SAP) or a mixture of a deodorant agent and a superabsorbent polymer,
   wherein the vaporization module comprises a syringe pump; a first stainless tube connected to a syringe tip of the syringe pump; a second stainless tube having a stainless line inserted therein; a heating band surrounding the second stainless tube; and a gas injection unit for injecting the carrier gas into the second stainless tube.

2. The apparatus according to claim 1, wherein a length of the heating band is 3 m or more.

3. The apparatus according to claim 1, wherein the collection module comprises an impinger and water accommodated in the impinger.

4. A method for quantitatively evaluating performance of a deodorant member using the apparatus of claim 1, the method comprising:
   heating an ammonia to vaporize it;
   adsorbing the vaporized ammonia to the deodorant member;
   desorbing the ammonia from the deodorant member by injecting a carrier gas into the deodorant member having the ammonia gas adsorbed therein for 5 minutes to 1 hour, and raising a temperature from 100° C. to 700° C. at a rate of 1 to 10° C./min; and
   collecting and quantitatively analyzing the desorbed ammonia gas through an impinger.

5. The method according to claim 4, wherein the quantitative analysis of the collected ammonia is performed using one or more selected from the group consisting of gas chromatography (GC)-thermal conductivity detector (TCD), GC-flame ionisation detector (FID), GC-electron capture detector (ECD), GC-mass spectrometry (MS) and ion chromatography.

6. A system for evaluating performance of the deodorant member, comprising the apparatus of claim 1.

7. The apparatus according to claim 1, wherein the deodorant agent comprises a porous adsorbent material, a zeolite, an aluminosilicate particle, an aluminosilicate particle carrying an organic acid, an activated carbon, zirconium phosphate, kate, a zinc oxide or a mixture thereof.

* * * * *